United States Patent

Nguyen et al.

[19]

[11] Patent Number: 5,873,462
[45] Date of Patent: Feb. 23, 1999

[54] PEN NEEDLE DISPENSER

[75] Inventors: Tuan V. Nguyen, Rockaway; Michael A. DiBiasi, West Milford; Robert E. West, Morristown, all of N.J.

[73] Assignee: Becton Dickinson and Company, Franklin Lakes, N.J.

[21] Appl. No.: 928,691

[22] Filed: Sep. 12, 1997

[51] Int. Cl.⁶ .................................................. B65D 83/02
[52] U.S. Cl. ..................... 206/366; 206/534; 220/502; 220/525
[58] Field of Search ................................. 206/536, 538, 206/539, 365, 366, 534, 459.5; 220/502, 507, 525

[56] References Cited

U.S. PATENT DOCUMENTS 4,555,044  11/1985  Pearo ........................................ 206/538
5,575,392  11/1996  Cutler ..................................... 206/536 X Primary Examiner—Jacob K. Ackun
Attorney, Agent, or Firm—Alan W. Fiedler

[57] ABSTRACT

A pen needle dispenser having a cover rotatably mounted on a circular shaped container having a plurality of cavities, with each cavity dimensioned to receive a pen needle assembly with or without shields. The cover includes a slot that is rotated into alignment with one of the cavities in the container to provide the user with access to one unused shielded pen needle and thereby permits the pen needle to be mounted on a medication delivery pen. After use the used unshielded pen needle is returned to and locked in the cavity. Then, the cover is rotated until the slot is aligned with another cavity containing the next unused shielded pen needle to be used during the next injection. The pen needle dispenser prevents the cover from rotating the slot back to cavities containing used pen needles.

11 Claims, 7 Drawing Sheets

PEN NEEDLE DISPENSER

BACKGROUND OF THE INVENTION

1. Field of the Invention

The subject invention relates to a pen needle dispenser and, more particularly, to an apparatus that holds and dispenses sterile pen needles for medication delivery pens and that safely stores the needles after use.

2. Description of Related Art

Hypodermic syringes are used to deliver selected doses of medication to patients. The prior art hypodermic syringe includes a syringe barrel having opposed proximal and distal ends. A cylindrical chamber wall extends between the ends and defines a fluid receiving chamber. The proximal end of the prior art syringe barrel is substantially open and receives a plunger in sliding fluid tight engagement. The distal end of the prior art syringe barrel includes a passage communicating with the chamber. A needle cannula is mounted to the distal end of the prior art syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior art hypodermic syringe often is stored in a vial having a pierceable elastomeric seal. Medication in the prior art vial is accessed by piercing the elastomeric seal with the needle cannula. A selected dose of the medication is drawn into the chamber of the syringe barrel by moving the plunger a selected distance in a proximal direction. The needle cannula is withdrawn from the vial, and the medication is injected into a patient by moving the plunger in a distal direction.

Some medication, such as insulin is self-administered. The typical diabetes patient will require injections of insulin several times during the course of the day. The required dose of insulin will vary from patient to patient, and for each patient may vary during the course of the day and from day to day. Each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard prior art hypodermic syringe and vial can be inconvenient and embarrassing in these public environments.

Medication delivery pens have been developed to facilitate the self-administration of medication. A prior art medication delivery pen is identified generally by the numeral 1 in FIG. 1. Pen 1 contains a cartridge with sufficient medication for several doses. The prior art cartridge has opposed proximal and distal ends. The distal end is closed by a pierceable and resealable rubber septum identified by the numeral 2 in FIG. 1. The proximal end receives a stopper in sliding fluid-tight engagement. The prior art cartridge is disposed in an elongate pen-like body 4 with a proximal end (not shown) and an opposed distal end 6. The proximal end of the pen body includes a plunger for selectively driving the stopper of the cartridge in the distal direction and a dose setting mechanism for determining the distance through which the plunger and stopper can move. Distal end 6 of pen body 4 includes an array of threads 8 for threaded engagement with a pen needle assembly 90. Pen needle assembly 90 includes a needle cannula 91 with opposed proximal and distal points 92 and 93 and a threaded mounting skirt 94 which surrounds the proximal tip 92. Mounting skirt 94 is threadedly engageable with threads 8 on distal end 6 of pen body 4. A safety shield 95 is releasably engaged over distal point 93 and portions of mounting skirt 94 to prevent accidental needle sticks.

A person who must periodically inject doses of medication will carry a medication delivery pen 1 and a supply of pen needle assemblies 90. Each pen needle assembly 90 has its needle cannula 91 safely and sterility sealed in its own shield 95, and is accessed immediately prior to administering a dose of medication. Pen needle assembly 90 then is mounted to distal end 6 of prior art pen 1. This mounting causes proximal point 92 of needle cannula 91 to pierce rubber septum 2 of the cartridge, to place needle cannula 91 in communication with the medication in pen 1. Pen 1 then is used to inject the selected dose of medication. After completing the injection, needle assembly 90 is separated from pen 1 and is discarded. Pen 1 may be used repeatedly in this manner until the medication is exhausted. Such prior art pens offer many conveniences and efficiencies. However, the storage of unused needles and the final disposal of used needles has presented problems. In particular, supplies of new needles often are loosely scattered in the bottom of purses or briefcases, and used needles are often disposed of unsafely.

SUMMARY OF THE INVENTION

The subject invention relates to a storing and dispensing apparatus for needle assemblies used with hypodermic syringes and preferably pen needles used with medication delivery pens.

The pen needle dispenser of the present invention includes a cover rotatably mounted on a container having a plurality of cavities, with each cavity dimensioned to receive a pen needle assembly with or without a shield. The cover includes a slot therethrough that is rotated into alignment with a cavity in the container that contains an unused shielded pen needle. When the slot is aligned with such a cavity, the user inserts the distal end of a medication delivery pen into the cavity to mount the unused shielded pen needle on the medication delivery pen. After the shield has been removed from the pen needle and the injection has been performed, the used unshielded pen needle is returned to the cavity using the medication delivery pen and is snap-locked in the cavity to allow the pen needle to be easily removed from the distal end of the medication delivery pen and prevent reuse of the pen needle. The user then rotates the cover until the slot in the cover provides access to the next cavity containing another unused shielded pen needle to be used during the next injection.

As noted above, one object of the present invention is to prevent the pen needle from being reused by having it locked and covered in the pen needle dispenser. In addition, once the cover has been rotated to the next cavity, the pen needle dispenser provides means to prevent the cover from rotating back to used pen needles.

Another object of the present invention is to provide a user with a convenient way to carry, dispose of and keep track of their personal pen needle usage. The pen needle dispenser will contain a predetermined number of pen needles in respective cavities, with each cavity being sealed by a numbered label or sterility membrane. The numbered labels will indicate how many unused pen needles remain in the pen needle dispenser.

Another object of the present invention is to provide a pen needle dispenser that can hold and dispense pen needles of different types that are, e.g., threaded or snapped onto the distal end of a medication delivery pen. By working with snap-on designed needles, the pen needle dispenser allows for a very simple push-pull motion to be used to attach and detach the pen needle assembly from the medication delivery pen.

Another object of the present invention is to allow the user to carry pen needle assemblies in one convenient dispensing mechanism and provide the user with a convenient and safe way to dispose of these used pen needle assemblies.

These and other aspects, features and advantages of the present invention will become apparent from the following detailed description taken in conjunction with the accompanying drawings.

DETAILED DESCRIPTION

Figure 1:
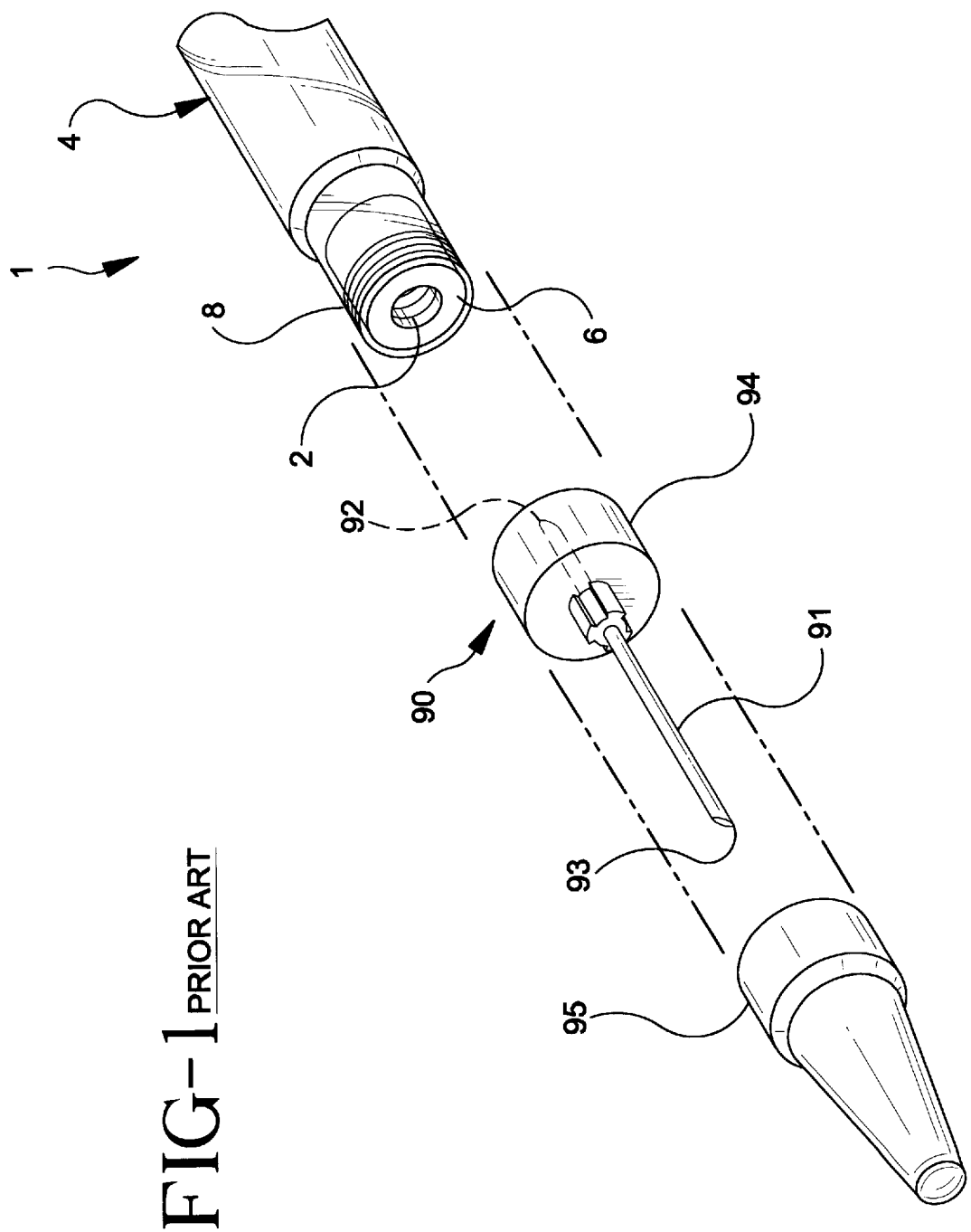
FIG. 1 is an exploded perspective view of a prior art pen needle and the distal end of a prior art medication delivery pen with which the present invention is intended to be used.
Figure 2:
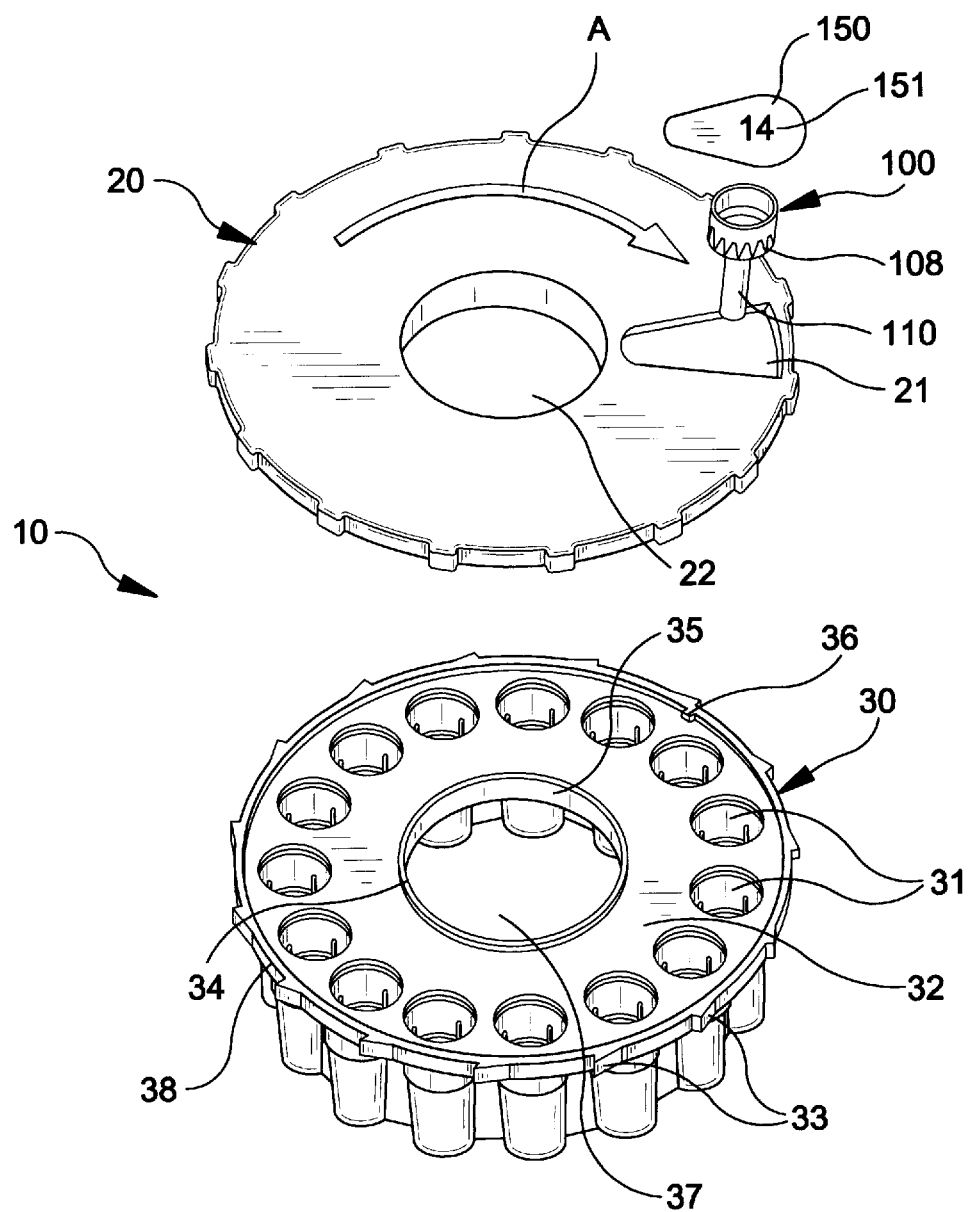
FIG. 2 is an exploded perspective view of a pen needle dispenser according to the present invention.
Figure 3:
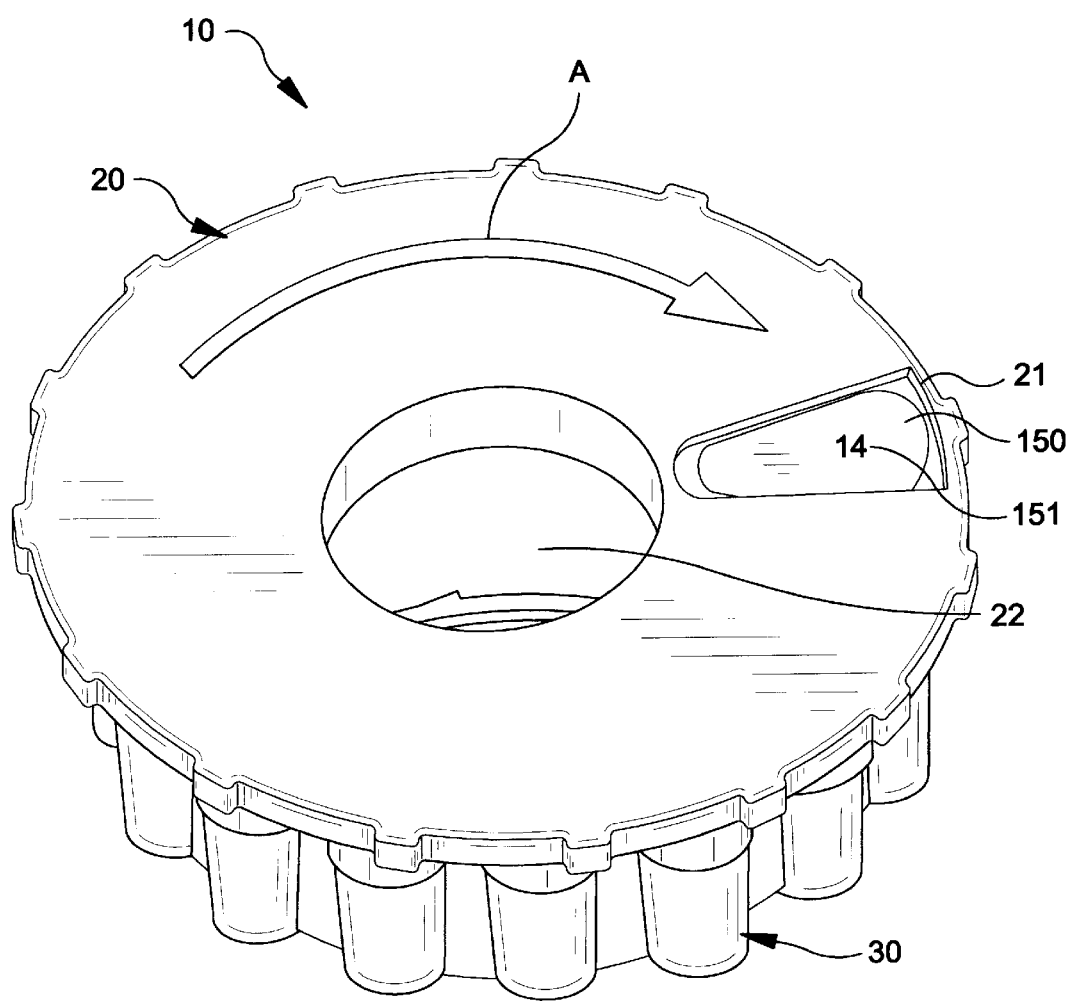
FIG. 3 is a perspective view of an assembled pen needle dispenser shown in FIG. 2.
Figure 5:
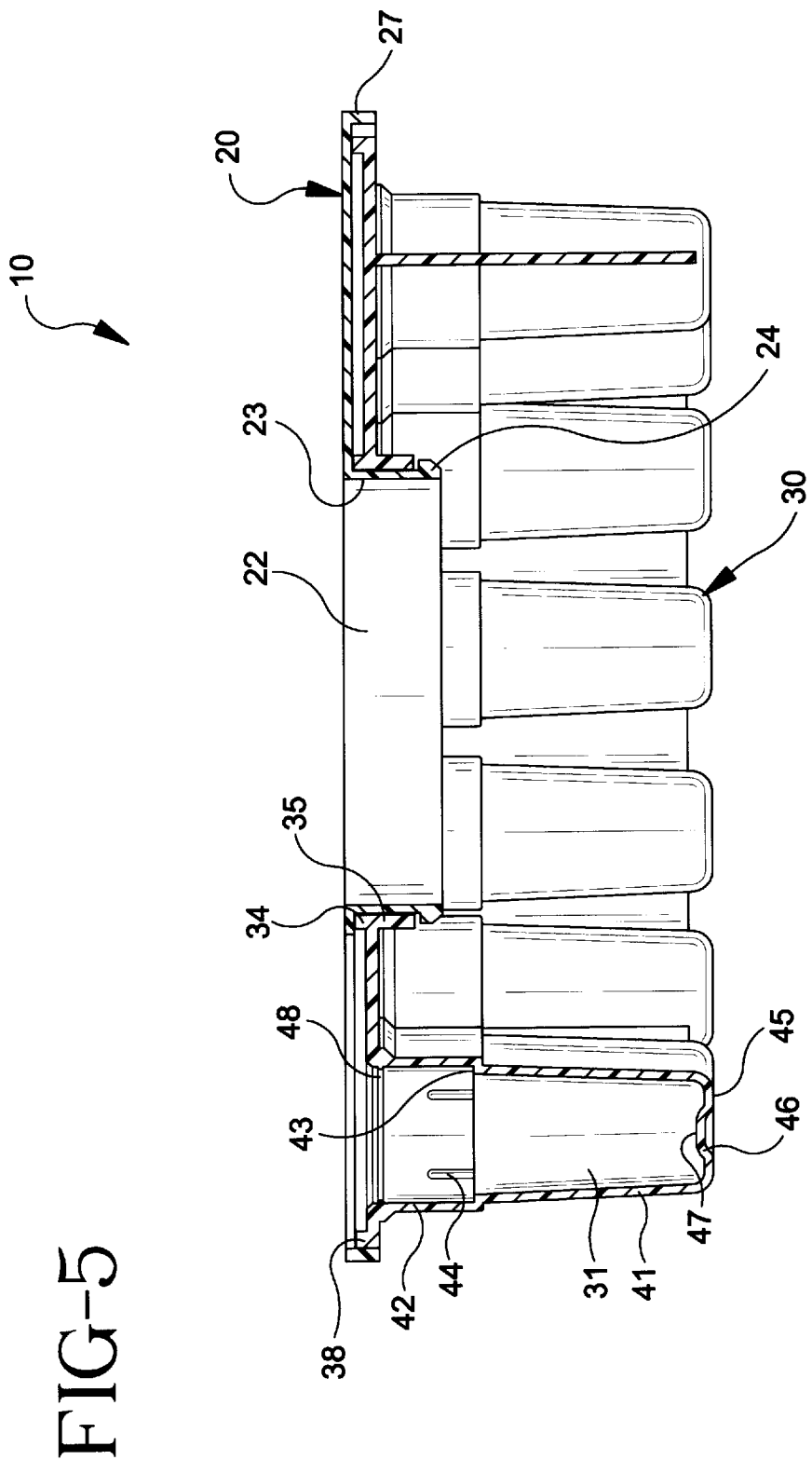
FIG. 5 is a cross-sectional view of the assembled pen needle dispenser shown in FIG. 3.

A pen needle dispenser in accordance with the subject invention is identified generally by the numeral 10 in FIGS. 2, 3 and 5. As shown in the exploded perspective view in FIG. 2, pen needle dispenser 10 includes a cover 20 and a container 30. Container 30 includes a plurality of cavities 31 about the circumference of container 30, with each cavity 31 being dimensioned to receive a pen needle assembly 100. Each pen needle assembly 100 is originally sealed in a respective cavity 31 using a label or sterility barrier 150 that is attached to an upper surface 32 of container 30, which provides sterility for the unused pen needle assemblies 100 contained in each cavity 31. Pen needle dispenser 10 is initially loaded with a predetermined number of pen needle assemblies 100 in respective cavities 31, with each cavity 31 being sealed by a label or sterility membrane 150 having a number 151 thereon. Number 151 or other indicia on label 150 indicates to the user how many unused pen needle assemblies 100 remain in pen needle dispenser 10.

An alternative design according to the present invention includes a label or sterility barrier 150 that does not need to be removed from upper surface 32 of container 30. That type of label 150 would be scored at the location of cavity 31, of course, without affecting the integrity of the seal and would allow for controlled breaking with the distal end of the medication delivery pen. The controlled breaking of the scored area would then allow the distal end of the medication delivery pen to be inserted through label 150 and into hub 102 on pen needle assembly 100 and threaded or snapped thereon.

Figure 4:
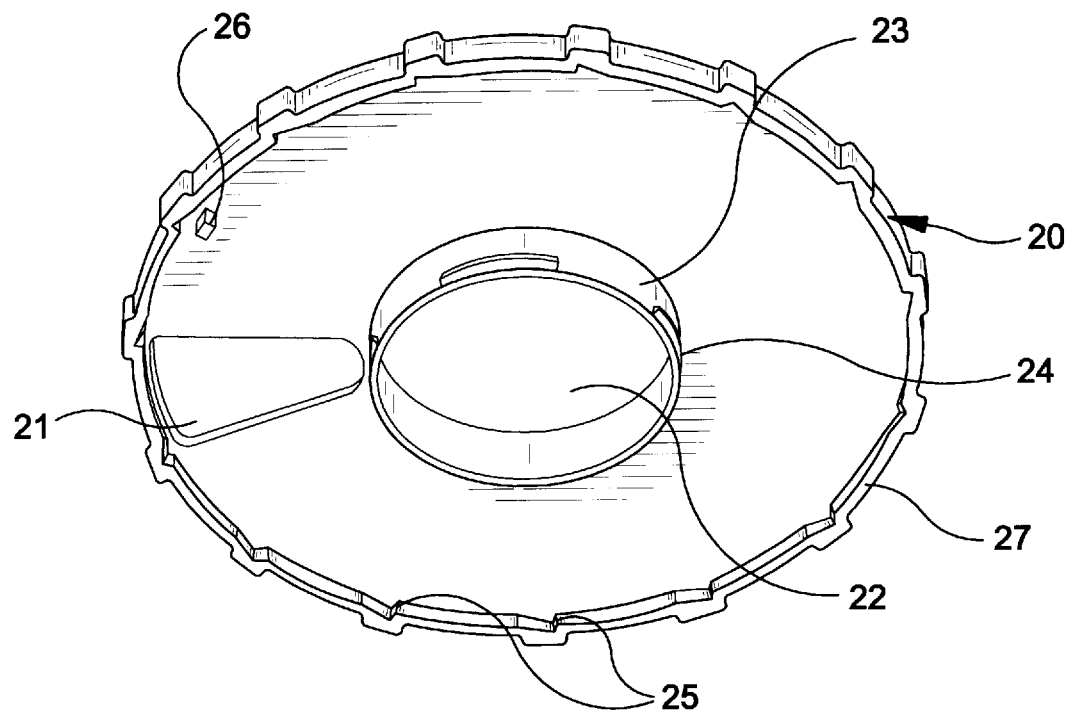
FIG. 4 is a perspective view of the underside of the cover of the pen needle dispenser shown in FIG. 2.

FIG. 3 is a perspective view of pen needle dispenser 1 fully assembled with cover 20 rotatably mounted on container 30 and label 150 attached to upper surface 32 over one of cavities 31. FIG. 3 also shows arrow "A" that indicates the direction a user should rotate cover 20 with respect to container 30 to move slot 21 over the next cavity 31. As more clearly shown in FIGS. 2, 4 and 5, container 30 includes a central opening 37 that is surrounded by an internal flange including an upper internal flange 34 and a lower internal flange 35 and an outer lip 38 around its outer circumference. Outer lip 38 includes a plurality of ratchet teeth 33 extending outwardly therefrom and an end of travel lock pin 36 extending from outer lip 38 in the direction of central opening 37. End of travel lock pin 36 is positioned on the opposite side of outer lip 38 from one of the ratchet teeth 33 and works with a similar end of travel lock key 26 located on the underside of cover 20 to stop rotation of cover 20 on container 30 when all cavities have passed under slot 21.

Cover 20 also includes a central opening 22 surrounded by an internal sleeve 23 that is connected to a plurality of retaining tabs 24. In addition, cover 20 includes an outer lip 27 around its circumference and a plurality of ratchet teeth 25 extending from outer lip 27 in the direction of central opening 22. As shown in FIG. 5, cover 20 is rotatably attached to container 30 by inserting internal sleeve 23 through central opening 37 in container 30 until retaining tabs 24 snap over lower internal flange 35. In the assembled arrangement shown in FIG. 5, when retaining tabs 24 snap over lower internal flange 35, cover 20 is attached to container 30 such that internal sleeve 23 rotates within upper and lower internal flanges 34 and 35. As shown in FIG. 5, upper internal flange 34 and outer lip 38 provide internal support for cover 20, which travels thereon during its rotation on container 30. When cover 20 is attached to container 30, ratchet teeth 33 extending from container 30 engage with ratchet teeth 25 extending into cover 20 and only permit cover 20 to rotate in the direction of arrow "A" or a clockwise direction. Therefore, cover 20 is not permitted to rotate in the counter-clockwise direction or to move slot 21 back over cavities 31 containing used unshielded pen needles 100.

Of course, when cover 20 is attached to container 30 it is important to locate end of travel lock key 26 on cover 20 adjacent to end of travel lock pin 36 on container 30, such that cover 20 can proceed with a full clockwise rotation on container 30. Therefore, when all cavities have been accessed using slot 21 on cover 20 and cover 20 has completed a complete clockwise rotation on container 30, end of travel lock key 26 on cover 20 will again be adjacent to end of travel lock pin 36 on container 30 but now will prevent further rotation in the clockwise direction, shown by arrow "A". In the current embodiment, cover 20 can never be rotated in the counter-clockwise direction on container 30 because of the above-described interaction of ratchet teeth 25 and 33.

Figure 6:
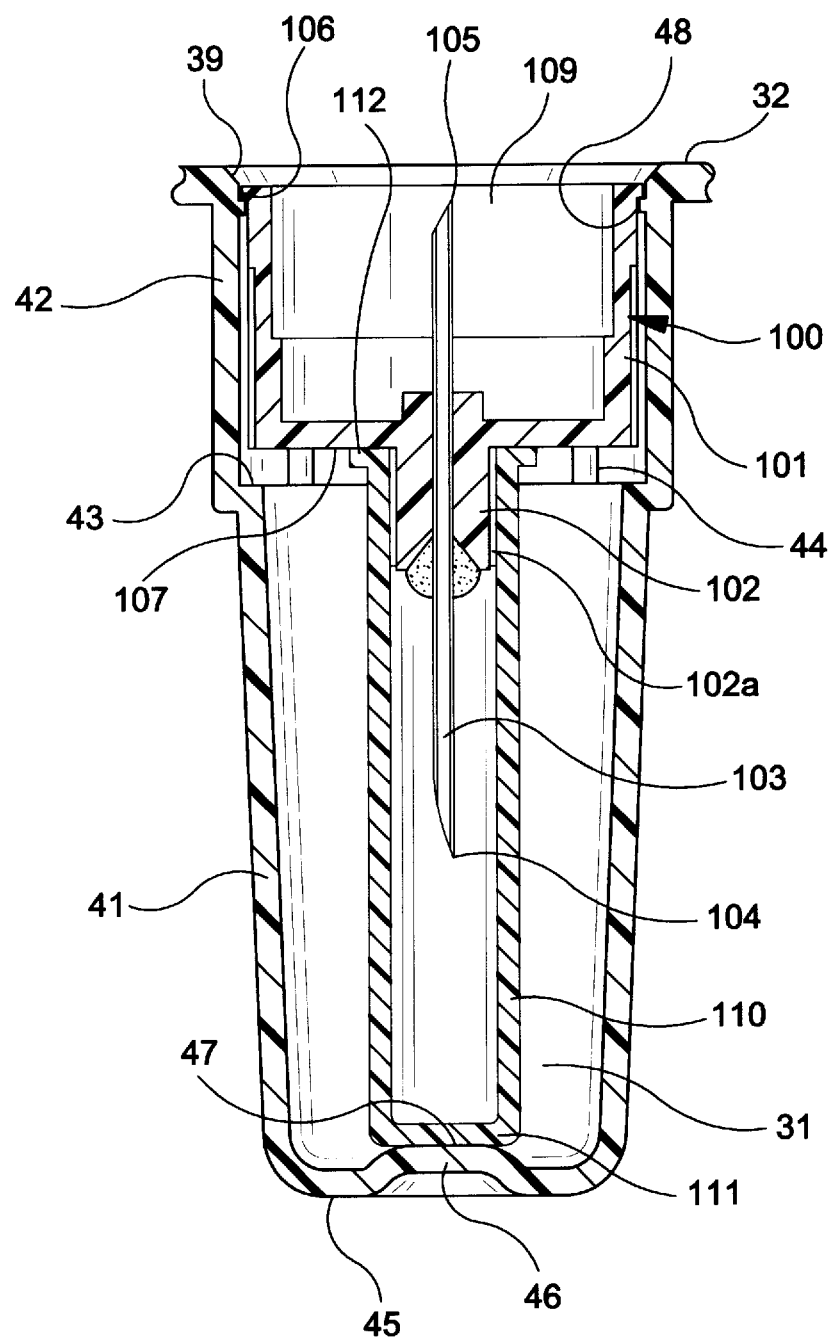
FIG. 6 is a cross-sectional view of a cavity containing an unused shielded pen needle in the pen needle dispenser shown in FIG. 2.

As described above, container 30 includes a plurality of cavities 31 around its circumference that are dimensioned to receive pen needle assemblies 100 with or without shields 110, shown in FIG. 2. As shown in FIG. 6, each cavity 31 includes a tapered opening 39 that guides the distal end of the medication delivery pen into cavity 31 for mating with pen needle assembly 100. Each cavity 31 also includes a bottom section 41 and an upper section 42, wherein bottom section 41 has a smaller diameter than upper section 42 with a shelf 43 formed where sections 41 and 42 meet. Upper section 42 includes a locking ring 48 and a plurality of laterally extending splines 44 therein that mate with a plurality of outer channels 108 on pen needle assembly 100, described further below. Bottom section 41 includes a closed bottom end 45 having a central recess 46 that forms an inner bottom surface 47 in bottom section 41.

Figure 7:
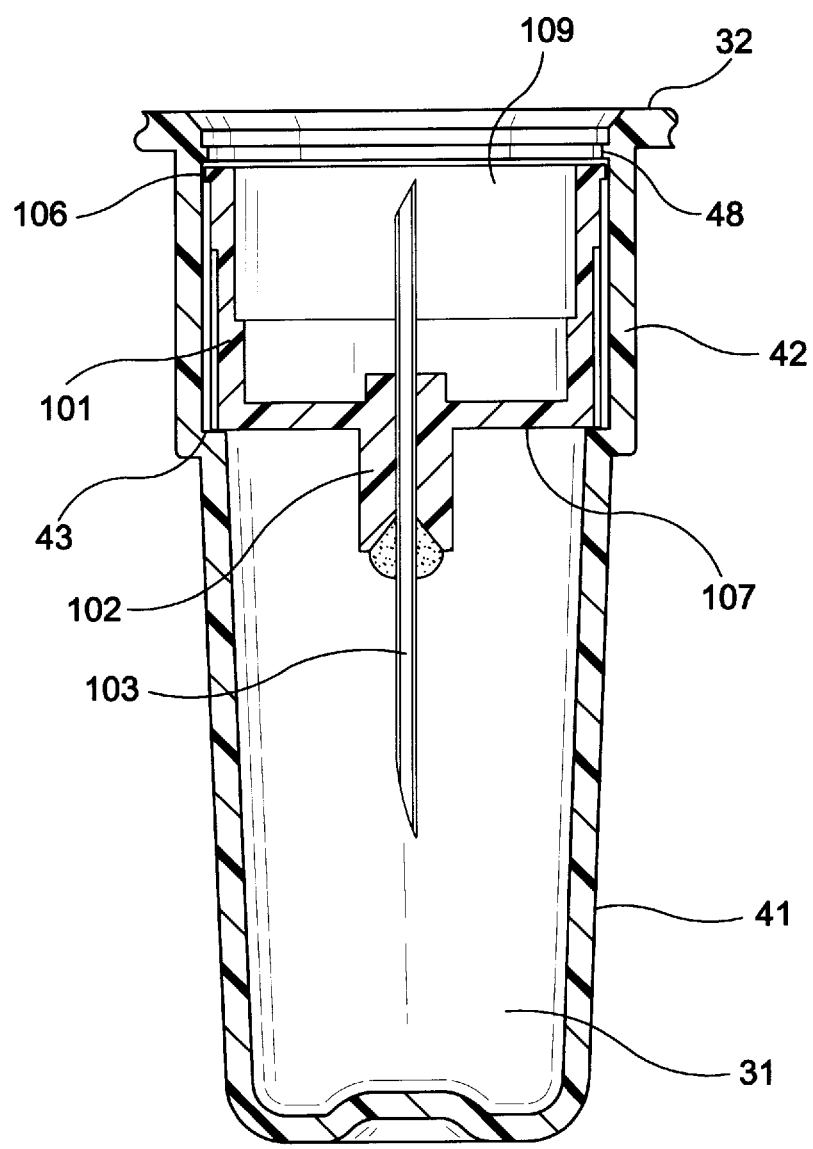
FIG. 7 is a cross-sectional view of another cavity containing a used unshielded pen needle locked in the pen needle dispenser shown in FIG. 2.

As shown in FIGS. 6 and 7, pen needle assembly 100 includes a skirt 101 having an open proximal end 109 and a distal end 107 having a hub 102 extending therefrom. A needle cannula 103 is mounted within hub 102 and includes a distal point 104 and a proximal point 105, wherein proximal point 105 is within skirt 101 and distal point 104 extends out of hub 102. Skirt 101 also includes a locking flange 106 extending from open proximal end 109. Pen needle assembly 100 also includes a plurality of tabs 102a extending from hub 102 that are dimensioned to be received within an open end 112 of a shield 110 when pen needle assembly 100 is originally assembled and loaded into pen needle dispenser 10, as shown in FIG. 6. Shield 110 also includes a closed distal end 111 that interacts with inner bottom surface 47 of cavity 31 to prevent pen needle assembly 100 from locking in cavity 31, as described below.

After shield 110 has been mounted on pen needle assembly 100 the assembled unit is inserted into cavity 31 until distal end 111 of shield 110 is stopped by inner bottom surface 47 on the inside of recess 46 at bottom end 45 of cavity 31. As shown in FIG. 6, in this arrangement, pen needle assembly 100 with attached shield 110 is slideably received with cavity 31 and can be easily removed since it is not locked or permanently retained therein except by label or sterility barrier 150, shown in FIG. 3, which is removed before pen needle assembly 100 is mounted on the medication delivery pen. In this arrangement, splines 44 in upper section 42 of cavity 31 engage respective outer channels 108 on skirt 101 of pen needle assembly 100 to prevent rotation of pen needle assembly 100 in cavity 31, which is important if pen needle assembly 100 is of the type having threads within skirt 101 that mate with threads on the distal end of the medication delivery pen. Of course, if the pen needle assembly 100 is of the type having a snap attachment, closed distal end 111 of shield 110 would prevent pen needle assembly 100 from moving into the locked position and locking in cavity 31 when the distal end of a medication delivery pen is snapped into skirt 101.

After use, the used and unshielded pen needle assembly 100 on medication delivery pen is inserted into tapered opening 39 of cavity 31 until distal end 107 of pen needle assembly 100 comes into contact with shelf 43 within cavity 31, the locked position, as shown in FIG. 7. In that position, locking flange 106 at the open proximal end 109 of skirt 101 has engaged locking ring 48 within cavity 31, which locks pen needle assembly 100 in cavity 31. At this point, the medication delivery pen can be extracted from skirt 101 by unthreading or unsnapping pen needle assembly 100 from the distal end of the medication delivery pen. Then, the user rotates cover 20 in the direction of arrow "A" until slot 21 is aligned with the next cavity 31 having a unused shielded pen needle 100 covered by another label 150.

As cover 20 is rotated in the direction of arrow "A" ratchet teeth 25 travel over one set of ratchet teeth 33 on container 30, which then prevents cover 20 from rotating in the direction counter to arrow "A". Of course, an alternative to the uni-directional cover shown in the drawings and described above would be a design that allows the user to rotate back to previously used needles. In that case, the other various features of the present invention could still be used on such a device. However, as described above and shown in the drawings, the current design would allow the user to repeatedly rotate cover 20 in the direction of arrow "A" to each cavity 31 until all of the pen needle assemblies 100 have been used and the last cavity 31 has been encountered by slot 21 on cover 20. That last cavity could be left empty so that the user will know that all pen needle assemblies 100 have been used and thereby indicate that pen needle dispenser 10 should now be properly disposed of. In addition, by providing an empty cavity 31 with all filled cavities 31 being fully enclosed behind cover 20, all the used pen needle assemblies 100 and their proximal points 105 would be protected from accidental needle sticks, since cover 20 would no longer be able to rotate in either direction. As explained above, further rotation in the direction of arrow "A" would be prevented by interaction between end of travel lock pin 36 on container 30 and end of travel lock key 26 on cover 20.

While the invention has been described with respect to a preferred embodiment, it is apparent that various changes can be made without departing from the scope of the invention as defined by the appended claims.

What is claimed is:

1. An apparatus for storing a plurality of needle assemblies and for selectively dispensing said needle assemblies therefrom, said apparatus comprising:
   a plurality of needle assemblies;
   a container having an upper surface including a plurality of cavities for receiving each of said plurality of needle assemblies therein;
   a cover rotatably mounted on said container, said cover having a slot that can be rotated into alignment with one of said plurality of cavities in said container to provide access through said cover to a needle assembly located in said one of said plurality of cavities;
   means preventing said needle assembly from moving into a locked position in said cavity; and
   means for locking said needle assembly in said cavity in the locked position.

2. An apparatus according to claim 1, further comprising means for preventing said cover from rotating on said container in a reverse direction while permitting said cover to rotate on said container in a forward direction to rotate said slot into alignment with one of said plurality of cavities in said container.

3. An apparatus according to claim 2, wherein said means for preventing rotation of said cover in said reverse direction includes a plurality of ratchet teeth on said cover that interact with a plurality of ratchet teeth on said container to prevent said cover from rotating on said container in said reverse direction after said slot is aligned with one of said plurality of cavities.

4. An apparatus according to claim 2, further comprising means for preventing said cover from further rotation in said forward direction after said slot has been rotated into alignment with each of said plurality of cavities in said container.

5. An apparatus according to claim 4, wherein said means for preventing said cover from further rotation in said forward direction includes an end of travel lock key on an inside surface of said cover that interacts with an end of travel lock pin on said upper surface of said container.

6. An apparatus according to claim 1, wherein:
   said cavity further comprises an upper section and a lower section having a smaller diameter than said upper section and a shelf located where said upper section is connected to said lower section, said lower section having a bottom end;
   said needle assembly includes a skirt having an open proximal end and a distal end that is connected to a hub with a double-ended needle cannula extending through said hub; and said means for preventing said needle assembly from moving into the locked position in said cavity includes:
  a recess extending into said bottom end of said lower section to provide a raised bottom surface in said bottom end; and
  a shield having a closed distal end and an open proximal end that is mounted on said hub of said needle assembly such that, when said shield is mounted on said hub and said shielded needle assembly is inserted into said cavity, interaction between said closed distal end of said shield and said raised bottom surface of said recess in said cavity prevent said needle assembly from moving into the locked position in said cavity.

7. An apparatus according to claim 6, wherein said upper section of said cavity further comprises a plurality of splines and said skirt of said needle assembly includes a plurality of outer channels that mate with said plurality of splines in said cavity to prevent said needle assembly from rotating within said cavity so that said needle assembly in said cavity can be threaded onto a medication delivery pen.

8. An apparatus according to claim 1, wherein:
said cavity further comprises an upper section and a lower section having a smaller diameter than said upper section and a shelf located where said upper section is connected to said lower section, said upper section having a tapered opening;

said needle assembly includes a skirt having an open proximal end and a distal end that is connected to a hub with a double-ended needle cannula extending through said hub; and said means for locking said needle assembly in said cavity in the locked position includes:
  a locking ring within said tapered opening of said cavity; and
  a locking flange around said open proximal end of said skirt of said needle assembly that snaps over said locking ring to lock said needle assembly in said locked position.

9. An apparatus according to claim 8, wherein said distal end of said skirt of said needle assembly contacts said shelf between said upper and lower sections in said cavity when said needle assembly is locked in said locked position.

10. An apparatus for storing a plurality of needle assemblies and for selectively dispensing said needle assemblies therefrom, said apparatus comprising:

a plurality of needle assemblies;

a container having an upper surface including a plurality of cavities for receiving said plurality of needle assemblies;

a sterility barrier comprising a plurality of removable labels with each of said removable labels covering one of said plurality of cavities; and a cover rotatably mounted on said container, said cover having a slot that can be rotated into alignment with one of said plurality of cavities in said container to provide access through said cover to a needle assembly located in said one of said plurality of cavities, wherein each of said plurality of removable labels includes an indicia that identifies the number of unused needle assemblies remaining in the apparatus.

11. An apparatus for storing a plurality of needle assemblies and for selectively dispensing said needle assemblies therefrom, said apparatus comprising:

a plurality of needle assemblies;

a container having an upper surface including a plurality of cavities for receiving said plurality of needle assemblies;

a sterility barrier over each of said plurality of cavities; and a cover rotatably mounted on said container, said cover having a slot that can be rotated into alignment with one of said plurality of cavities in said container to provide access through said cover to a needle assembly located in said one of said plurality of cavities, wherein said sterility barrier includes scoring over each of said plurality of cavities to permit said sterility barrier to be pierced by a medication delivery pen accessing said cavity behind said scoring.

* * * * *